US005665062A

United States Patent [19]

Houser

[11] Patent Number: 5,665,062
[45] Date of Patent: Sep. 9, 1997

[54] ATHERECTOMY CATHETER AND RF CUTTING METHOD

[76] Inventor: Russell A. Houser, 4572 Maureen Cir., Livermore, Calif. 94550

[21] Appl. No.: 376,226

[22] Filed: Jan. 23, 1995

[51] Int. Cl.$^6$ ............................................. A61B 17/00
[52] U.S. Cl. ............................................. 604/22
[58] Field of Search ................... 604/22; 606/159, 606/170, 171, 180; 128/751–755

[56] References Cited

U.S. PATENT DOCUMENTS

| | | | |
|---|---|---|---|
| 4,793,359 | 12/1988 | Sharrow . | |
| 5,009,659 | 4/1991 | Hamlin et al. . | |
| 5,078,722 | 1/1992 | Stevens | 604/22 |
| 5,078,723 | 1/1992 | Dance et al. . | |
| 5,085,662 | 2/1992 | Willard . | |
| 5,087,256 | 2/1992 | Taylor et al. . | |
| 5,087,265 | 2/1992 | Summers . | |
| 5,098,431 | 3/1992 | Rydell . | |
| 5,100,426 | 3/1992 | Nixon . | |
| 5,171,255 | 12/1992 | Rydell | 606/170 |
| 5,222,966 | 6/1993 | Perkins et al. | 606/170 |
| 5,242,460 | 9/1993 | Klein et al. | 604/22 |
| 5,284,486 | 2/1994 | Kotula et al. | 606/170 |
| 5,312,425 | 5/1994 | Evans et al. . | |
| 5,366,463 | 11/1994 | Ryan | 604/22 |
| 5,395,313 | 3/1995 | Naves et al. | 604/22 |
| 5,441,510 | 8/1995 | Simpson et al. | 604/22 |
| 5,514,115 | 5/1996 | Frantzen et al. | 606/170 |

*Primary Examiner*—Manuel Mendez
*Attorney, Agent, or Firm*—Frederick W. Niebuhr, Esq.; Haugen and Nikolai, P.A.

[57] ABSTRACT

An atherectomy device includes a catheter with a window at its distal tip for admitting tissue into a catheter compartment. A cylindrical cartridge in the compartment has a cutting edge that supports an electrically conductive cutting element, e.g. a band or wire. The cutting element and adjacent tissue can be heated to a selected temperature by generating an electrical current through the cutting element. The catheter is maneuverable to position its distal end near a lesion in an artery. The catheter incorporates a dilatation balloon or other feature to urge the catheter against the lesion, so that at least part of the lesion enters the compartment through the window. Then, the cartridge is manipulated from the catheter's proximal end to move the cutting edge across the window, severing the acquired tissue. According to alternative embodiments, the cartridge is either rotated or moved axially relative to the catheter, in either event closing the catheter window when the cut is complete. Further alternatives involve either placing an indifferent electrode on the patient and providing an RF signal via a single conductor to the cutting element for ohmic heating, or providing an RF (or a DC) current through the cutting element and two separate conductors for direct resistive heating of the cutting element.

30 Claims, 3 Drawing Sheets

ATHERECTOMY CATHETER AND RF CUTTING METHOD

BACKGROUND OF THE INVENTION

The present invention relates to devices for removing obstructions from body lumens, and more particularly to catheters for removing atherosclerotic plaque and thrombotic occlusions from blood vessels.

Atherectomy catheters are known for their utility in removing atherosclerotic plaque and thrombotic occlusions from arteries. While intended mainly for use in the coronary arteries, such catheters may as well be used in peripheral vessels. Beyond coronary uses, such catheters can have neurological applications, e.g., removal of lesions in carotid arteries, gynecological use in recanalizing fallopian tubes, and a potential urological application for removal of benign prostate hyperplasia.

Atherectomy catheters have a variety of designs. According to one design, the catheter has a rounded or bullet shaped tip with an abrasive surface. At the treatment site, the tip is rotated at high speed and burrows through the occlusion. The resulting debris, typically in particulate form, is not captured by the device. Rather, it is allowed to flow to the capillary bed where it is absorbed. The device is most effective in abrading hardened (calcified) occlusions, with the intent being to produce particulate debris no larger than about 7 microns in diameter. When encountering softer occlusions, however, the device presents the risk of an occlusion breaking off during the atherectomy procedure, causing an acute and potentially life-threatening reclosure of the artery. The abrasive tip may inadvertently remove endothelium cells during catheter insertion, use or removal, thereby creating sites for potential lesions.

A second type of catheter employs a cartridge housed within the catheter, near the catheter distal tip. When the distal tip region is placed near the occlusion, plaque enters the cartridge through an opening or "cutting window". A cup-shaped blade then is rotated or oscillated at high speed, and advanced to cut and capture plaque that entered the cartridge. U.S. Pat. No. 5,312,425 (Evans); U.S. Pat. No. 5,087,265 (Summers); and U.S. Pat. No. 5,085,662 (Willard) disclose versions of atherectomy catheters with a movable blade or cartridge within a tissue collection volume near the catheter distal tip.

An example of an atherectomy catheter that depends on vaporization of plaque is found in U.S. Pat. No. 5,087,256 (Taylor). A dome-shaped head on the tip can be heated to temperatures in the range of 300–400 degrees C., for disintegrating plaque. U.S. Pat. No. 5,098,431 (Rydell) discloses a catheter in which an RF discharge between two spaced apart annular electrodes, electrosurgically cuts tissue to remove a blockage.

Conventional atherectomy catheters are limited principally to an axial cutting direction and subject to smooth cell muscle migration (restonosis) after treatment. Patients treated with conventional atherectomy devices have restonosis rates of 30–40 percent within the six months following treatment.

Therefore, it is an object of the present invention to provide an atherectomy catheter with a cutting edge that achieves a finer, more accurate cutting of unwanted tissue, to reduce the risk of acute blockage due to the breaking off of an occlusion.

Another object is to provide a tissue cutting element for an atherectomy catheter that is effective in severing calcified and soft occlusions.

A further object is to provide a flexible atherectomy catheter that incorporates means for capturing tissue being severed, to ensure against the escape of such tissue into the blood stream.

Yet another object is to provide an atherectomy catheter with enhanced versatility, due to the incorporation of longitudinal and transverse (arcuate) tissue cutting motions.

Further, it is an object of the present invention to provide an atherectomy catheter and procedure tending to seal the region of the cut, thus tending to reduce the incidence of restonosis.

SUMMARY OF THE INVENTION

To achieve these and other objects, there is provided a device for removing atheromas from a body lumen. The device includes an elongate catheter having a proximal end and a distal end. The catheter has a wall that defines a compartment within the catheter near its distal end, and a window is formed through the catheter wall to allow entry into the compartment. The catheter incorporates an electrically conductive tissue cutting element. A means is provided for generating an electrical current in the cutting element to heat the cutting element and adjacent tissue at least to a selected temperature above normal body temperature (i.e. 37 degrees C.). A carrier is mounted movably relative to the catheter, for supporting the cutting element proximate the window and for a controlled movement of the cutting element along and adjacent the window. The catheter is flexible and maneuverable to locate its distal tip within a body lumen and to place the window against a tissue wall segment of the body lumen to acquire tissue within the compartment. The cutting element, when heated and when undergoing the controlled movement, severs the acquired tissue.

There are several suitable approaches for generating the current necessary for cutting. At present, the most preferred approach involves a biocompatible cutting element (e.g. of platinum) subjected to RF energy in combination with an indifferent plate electrode on the patient's back. Application of the RF energy causes ohmic heating of tissue near the cutting element as current passes through the tissue.

As an alternative, RF energy can be applied to heat an electrically resistive cutting element formed of nickel or a nickel chromium alloy. In this approach, the cutting element is heated to a temperature sufficient to sever a lesion that comes into contact with the element. As a third and presently least preferred alternative, DC power is applied to heat an electrically resistive cutting element, again of nickel or a nickel chromium alloy. For biocompatability, an insulative jacket or coating is applied to the nickel or nickel chromium cutting element.

The preferred cutting element is a flat band, having a thickness of about 0.015 inches and a substantially greater width. The band achieves a highly accurate and fine cut of the tissue, considerably reducing the pulling and tearing of tissue as compared to the conventional oscillating or rotating blades. Unwanted tissue is severed more cleanly, reducing patient risk. Further, it is believed that the elevated temperatures of the band and adjacent tissue have a sealing or cauterizing effect along the region of the cut. This is believed to result in a substantial reduction in restonosis in the treated artery.

As an alternative to a flat band, the cutting element can be a fine wire having a diameter of about 0.030 inches or less to provide the cutting edge.

The carrier preferably includes a cartridge contained within the compartment. The cartridge can have an axially

3 extended cartridge wall, a cartridge opening and a cutting edge along the cartridge opening for supporting the cutting element. A control means is coupled to the cartridge proximal end, and operable to selectively position and move the cartridge within the compartment, to provide the controlled movement of the cutting element. Preferably the cartridge wall is longer axially than the window, so that the cartridge can be positioned to substantially close the window and thus capture severed tissue. With tissue secured in this manner, there is no need for a suction device or other means to withdraw tissue proximally through the catheter immediately after it is cut. With no need to pay attention to a vacuum or suction means, the physician is able to direct more attention to the atherectomy procedure at hand.

Conversely, a vacuum means (or alternatively a plunger device and a diaphragm valve) may be provided if desired for removing severed tissue from the compartment, to allow cutting and removal of tissue at several locations during a single procedure.

There are several alternatives for supporting the cutting element. For example, the cutting edge can be the leading or distal edge of the cartridge, preferably but not necessarily annular. In this event, the cartridge is moved distally to provide the necessary controlled movement of the cutting element. Alternatively, the cutting edge can be an axial edge of the cartridge opening, in which event the cartridge is rotated about a longitudinal axis to move the cutting element in an arcuate path.

A preferred control means includes an elongate drive member, e.g. a rod, coil or tube, attached to the proximal end of the cartridge and extending proximally to a proximal end of the catheter. The member can be rotated, pushed or pulled at the catheter proximal end, to impart like motion to the cartridge.

Another aspect of the invention is a process for removing tissue from a body lumen, according to the following steps:

a. providing, near a distal end of an elongate catheter, a compartment and a window to the compartment through a catheter wall, and an electrically conductive tissue cutting element mounted to the catheter for a controlled movement of the cutting element adjacent and along the window;

b. inserting the catheter into a body lumen, and guiding the catheter to position the window against a tissue wall segment of the body lumen, thus to cause tissue to enter the compartment via the window and occupy the compartment;

c. generating an electrical current in the cutting element to heat the cutting element and adjacent tissue at least to a selected temperature above normal body temperature, while causing the cutting element to undergo the controlled movement, thereby to sever the tissue occupying the compartment.

After the tissue is severed, the compartment can be closed to prevent egress of the severed tissue. The controlled movement of the cutting element can be one of two alternatives: substantially linear and axial with respect to the catheter, or arcuate about an axis running longitudinally of the catheter.

Thus in accordance with the present invention, there is provided an atherectomy device and procedure suitable for treating soft occlusions and calcified occlusions alike, with clean and accurate cutting that reduces the risk of tissue tearing and escaping into the blood vessel under treatment. The catheter is versatile, due to its flexibility for traversing tortuous vessels and for the ability to cut in either an arcuate or axial path. The application of heat is concentrated along the region of the cut, i.e. the cutting element and adjacent tissue, reducing the required cutting force, increasing cutting accuracy and tending to cauterize or seal the region of the cut, thus tending to substantially prevent restonosis.

IN THE DRAWINGS

For a further understanding of the above features and advantages, reference is made to the following detailed description and to the drawings, in which.

Figure 1:
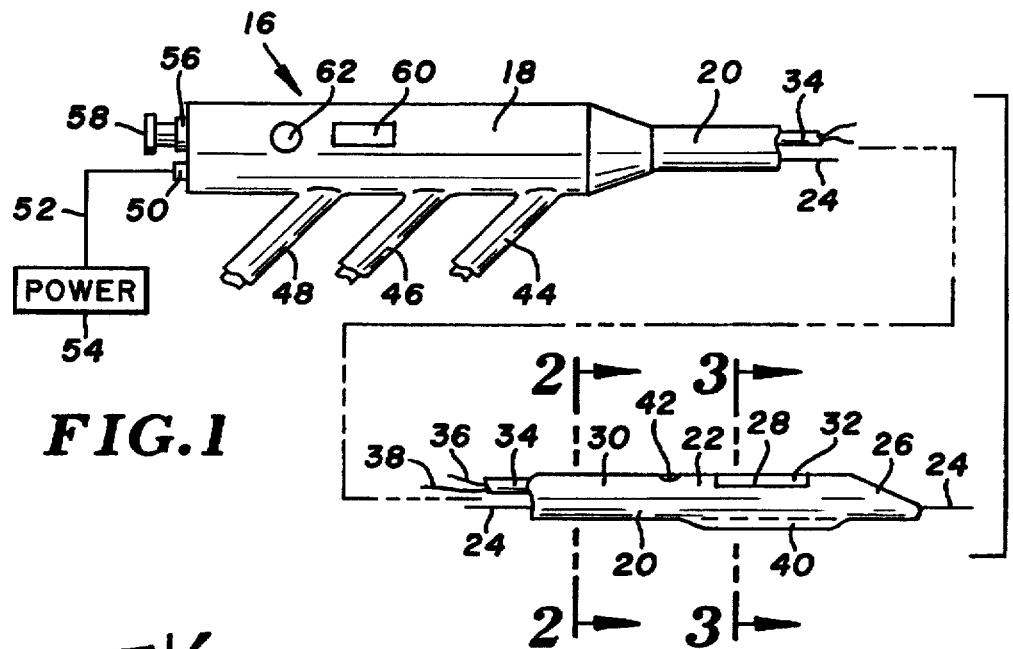
FIG. 1 is an elevation of an atherectomy device constructed in accordance with the present invention.
Figure 2:
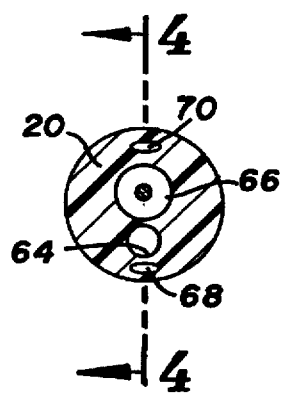
FIG. 2 is a sectional view taken along the line 2—2 in FIG. 1.
Figure 3:
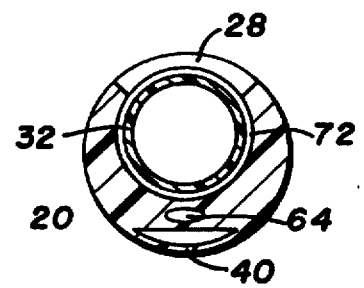
Figure 4:
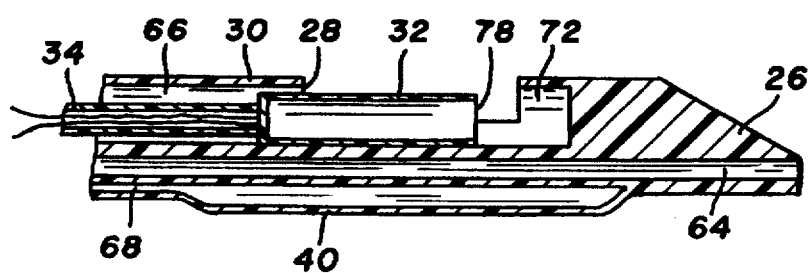
Figure 5:
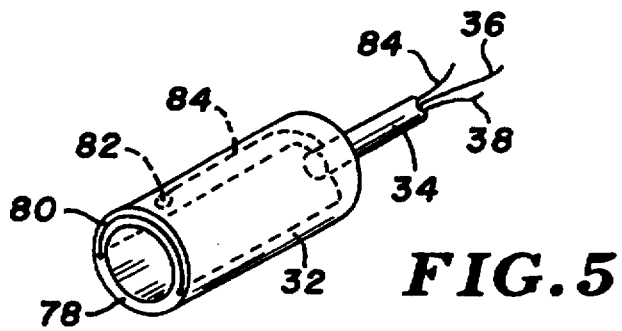
Figure 6:
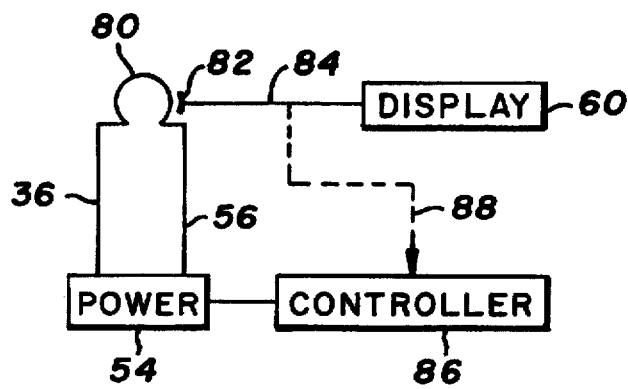
Figure 7:
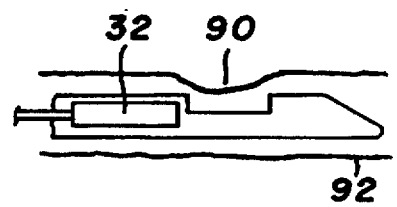
Figure 8:
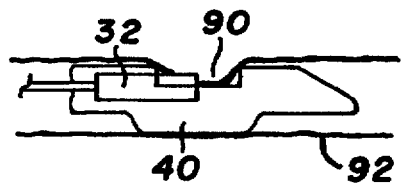
Figure 9:
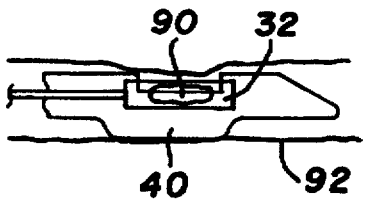
Figure 10:
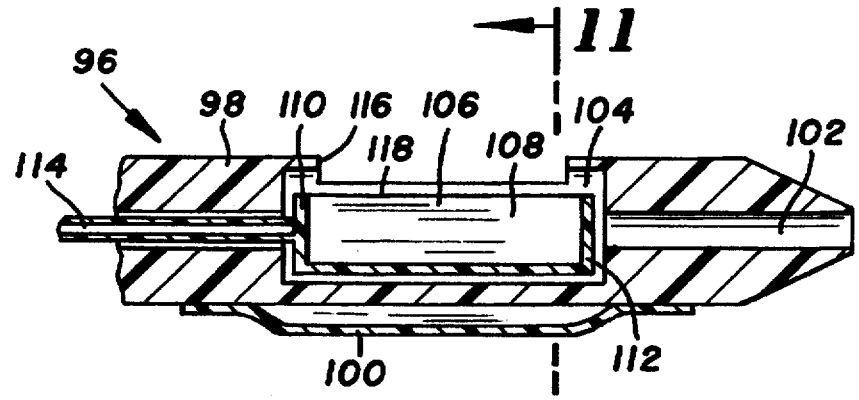
Figure 11:
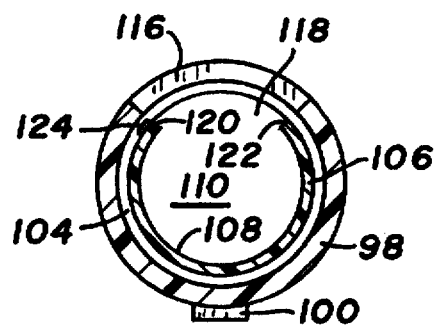
Figure 12:
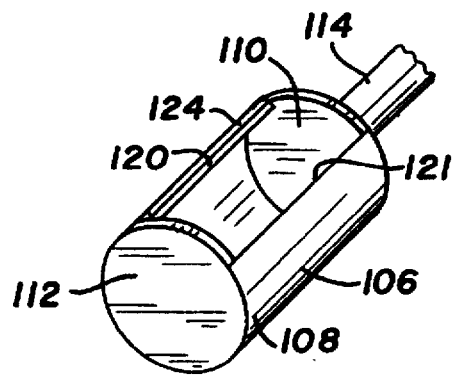
Figure 13:
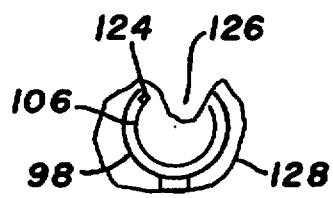
Figure 14:
Figure 15:
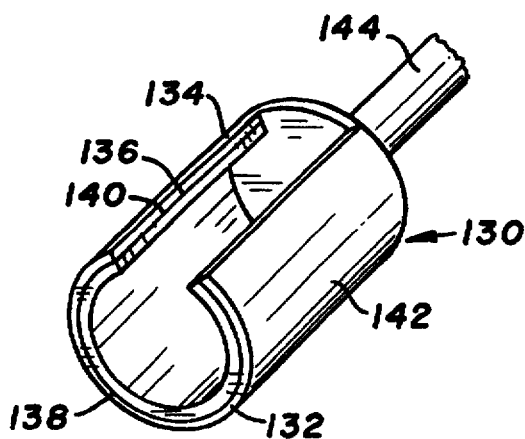
Figure 16:
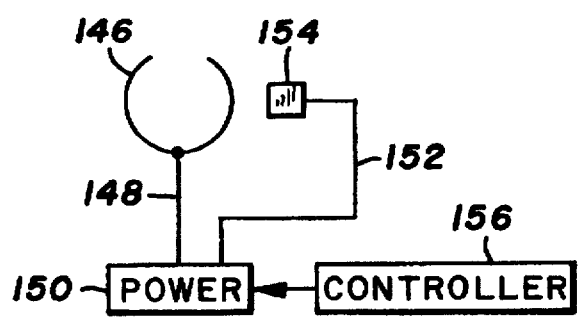

FIGS. 3 and 4 are sectional views taken along the lines 3—3 in FIG. 1 and 4—4 in FIG. 2;

FIG. 5 is a perspective view of a tissue retaining cartridge employed in the device;

FIG. 6 is a schematic view illustrating circuitry for providing an electrical current through a mounted heating element on the cartridge;

FIGS. 7–9 are diagrammatic views illustrating use of the device;

FIG. 10 is an elevational view of the distal end region of an alternative atherectomy device constructed according to the invention;

FIG. 11 is a sectional view taken along the line 11—11 in FIG. 10;

FIG. 12 is a perspective view of a tissue retaining cartridge used in the device of FIG. 10;

FIGS. 13 and 14 diagrammatically illustrate use of the device of FIG. 9;

FIG. 15 is a three-dimensional illustration of an alternative embodiment cartridge; and FIG. 16 is a schematic view of an alternative circuit for heating the cutting element.

DETAILED DESCRIPTION OF THE PREFERRED EMBODIMENTS

Turning now to the drawings, there is shown in FIG. 1 an atherectomy device 16 for removing unwanted tissue from body lumens, more particularly blood vessels. The device includes a control housing or handle 18, and an elongate and pliable catheter 20 connected at its proximal end to the handle.

Catheter 20 is formed of a biocompatible polymer such as Pebax (brand name) polyether block amides, Pellethane (brand name) polyurethane or polyimide, and can have an outside diameter in the range of 3 Fr. (1 mm) to 8 Fr. (2.7 mm) or larger. Catheter 20 includes several lumens that run axially from handle 18 to a distal end region 22. A guidewire 24, contained within one of the lumens, extends proximally beyond handle 18 and distally beyond a tapered distal tip 26 of the catheter. Further lumens are provided in the catheter, for delivery of contrast fluid or treatment fluid to the distal end region, and for balloon inflation. While not shown, a braided or other filament structure can be embedded into the catheter body to enhance torque transmission, if desired.

A window 28 is formed through a wall 30 of the catheter along the distal end region. Window 28 is elongate in the axial direction and extends along about forty percent of the circumference of catheter wall 30. A cartridge or cutting sleeve 32 is contained within catheter 20. The cartridge is shown adjacent and along window 28, but is movable axially relative to the catheter. This enables a proximal retraction of the catheter from window 28, to open the window whereby the catheter can acquire tissue. An elongate drive rod 34, contained within a lumen of catheter 20, is coupled to the proximal end of cartridge 32 and extends proximally through the catheter and into handle 18.

Drive rod 34 is formed of an electrically insulative material, e.g. a PTFE coated wire coil or spiral wrapped polyimide. The drive rod has a high degree of bending elasticity to permit its movement (with the remainder of catheter 20) along serpentine passages toward an intended treatment site. At the same time, drive rod 34 is sufficiently rigid in the axial direction to permit controlling the cartridge axial position by manipulating the drive rod at its proximal end. Drive rod 34 is constructed of an electrically insulated material. A pair of conductors 36 and 38, preferably polyimide jacketed copper or copper-clad steel wires, are bonded to the drive rod and electrically isolated from one another. Conductors 36 and 38 extend along the entire catheter length to control housing 18.

A dilatation balloon 40 is formed to extend axially along distal end region 22, axially aligned with window 28 but also spaced apart angularly 180 degrees, i.e. on the opposite side of the catheter from the window. Balloon 40 is inflated using a fluid supplied to the balloon under pressure via a lumen of catheter 20.

A fluid port 42 admits contrast or treatment fluids in the region just proximally of window 28, while such fluids can be administered distally of the window via the guidewire lumen.

Control housing 18 includes three branches for coupling two sources of fluid (not shown): a branch 44 for balloon inflation, and two branches 46 and 48 for delivery of contrast fluids or treatment fluids such as heparin. At the proximal end of the control housing is a connector 50 with two electrically independent paths coupled to conductors 36 and 38, respectively. A line 52 (e.g. coaxial) removably electrically couples connector 50 to a power supply 54. Power supply 54 preferably is an RF source, but can be a DC source as well. Also mounted at the housing proximal end are a fitting 56 and a control knob 58. Knob 58, coupled to the proximal end of drive rod 34, is movable axially relative to fitting 56, to control the axial position of cartridge 32.

A display 60 (e.g. LED) indicates the temperature of a cutting element mounted to the cartridge. A temperature control 62 adjusts the current through the cutting element, thus to set the cutting element temperature.

FIG. 2 shows several lumens running through the catheter, including a guidewire lumen 64 that also can be used to administer contrast and treatment fluids. A control lumen 66 accommodates drive rod 34. Further lumens include a balloon inflation lumen 68 and an upper infusion lumen 70 for providing fluids to fluid port 42.

As seen in FIGS. 3 and 4, control lumen 66 along the distal end region forms a compartment 72 to accommodate cartridge 32. The compartment extends distally beyond window 28 a slight distance, and extends proximally of the window a sufficient amount to allow cartridge retraction, i.e. placing the complete cartridge proximally of the window.

Cartridge 32 is cylindrical, having an axial wall 74 and a disk-shaped proximal wall 76. As seen in FIG. 5, cartridge 32 is open at its distal end to provide a circular cutting edge 78. A tissue cutting element, more particularly a fine, flat band 80, is mounted to the cutting edge to form an arc. Band 80 need not circumscribe the cutting edge, but should extend a sufficient amount to span window 28. Band 80 has a thickness of about 0.015 inches, and is formed of nickel or a nickel chromium alloy coated for biocompatability. Alternatively (in an indifferent electrode approach discussed below) the band can be formed of platinum or another electrically conductive and body compatible material. The band is heated when subject to an electrical current. As an alternative to the band, the cutting element can be a wire with a diameter of at most 0.030 inches.

The polymer forming cartridge 32 can be blended with barium sulphate, bismuth trioxide or another suitable radiopaque material to facilitate fluoroscopic observation of the cartridge position before and during tissue removal. Radiopaque markers also may be placed along the cartridge cutting edge and on corresponding (distal and proximal, or intermediate) edges of the window. Along with aiding accurate positioning, these markers are useful in confirming when the cartridge is closed after cutting.

Conductors 36 and 38 are coupled to opposite ends of cutting element 80. As indicated in broken lines, conductors 36 and 38 are embedded in axial wall 74 which, like the drive rod, is electrically insulative. A thermocouple 82 can be mounted to the cartridge near cutting edge 78 and preferably bonded to cutting element 80, to monitor the cutting element temperature. Conductors 84, embedded in the cartridge and the drive rod, permit the cutting element temperature to be monitored from control housing 18. Alternatively, thermistors can be used to sense temperature. Further, for a resistive cutting element (i.e. nickel or nickel chromium) a characteristic dependence of resistance upon temperature can be used to monitor the cutting element temperature.

Tissue is cut by advancing cartridge 32 distally from the retracted position, with cutting element 80 and adjacent tissue maintained at at least a predetermined temperature above body temperature. A circuit for heating the cutting element and tissue is schematically illustrated in FIG. 6. A controller 86 adjusts power from supply 54 as required, for generating current through cutting element 80 in an amount selected to heat the cutting element to the predetermined temperature. Thermocouple 82 senses the temperature and provides the corresponding temperature reading at display 60. If the display indicates a need to increase or reduce the temperature, controller 86 is adjusted to alter the current accordingly. A broken line at 88 indicates that if desired, the output of thermocouple 82 can be employed to automatically adjust the cutting element current.

The use of device 16 to remove unwanted tissue is shown in FIGS. 7-9, where catheter 20 has been either steered or moved over guidewire 24 to a treatment position near a lesion 90 in a coronary artery. Catheter 20 is manipulated from housing 18 to axially and angularly align the catheter and lesion 90, so that window 28 faces the lesion (FIG. 7). At this point, dilatation fluid is supplied to expand balloon 40 against an arterial wall 92 opposite the lesion (e.g. as in aforementioned U.S. Pat. No. 5,085,662). Balloon dilatation drives the catheter distal end upward as viewed in FIGS. 7-9, forcing the catheter against the arterial wall about lesion 90 and causing at least a portion of the lesion to enter compartment 72 through window 28.

With tissue thus acquired, cartridge 32 is advanced distally from the retracted position, while cutting element 80 is maintained at the selected temperature, from 50-600 degrees C. and more preferably 50-400 degrees C. This heating of the wire and adjacent tissue considerably enhances the cutting of tissue. Moreover, the heating has a cauterizing effect at the region of the cut and thus tends to seal the wound almost immediately after cutting, to significantly reduce smooth cell muscle migration or restonosis after treatment. The minute filament results in a precise, well defined cutting path that minimizes stretching and tearing of tissue. Accordingly, cutting element is effective in severing soft tissue as well as calcified or hardened tissue. This minimizes the risk of tissue fragmenting into particles or pieces that escape into the bloodstream.

Cartridge 32 is advanced until cutting edge 78 is distally of window 28 (FIG. 9), to completely acquire severed tissue within the cartridge. During or following the cut, a treatment fluid may be administered through lumens 64 and 70. After balloon deflation, the cartridge can be proximally withdrawn to remove the severed tissue.

In addition to the cauterizing/sealing effect, a salient feature of the invention is the continuity of axial wall 74, which closes window 28 when the cartridge is completely advanced. This insures that severed tissue remains captured within compartment 72 as the catheter is withdrawn, thus to eliminate the risk that severed tissue will enter the bloodstream.

FIG. 10 illustrates, in axial (longitudinal) section, the distal end region of an alternative device 96. This device differs from device 16 in several respects concerning primarily the catheter distal end, but also as to the manner of controlling the cartridge. A catheter 98 of device 96 has flexible band 100 along its distal end in lieu of a dilatation balloon. Band 100 can be flexed radially away from the catheter and, upon contacting an artery, drives the catheter toward the opposite end of the artery. An example of such band and its control is found in U.S. Pat. No. 5,087,265 (Summers).

A single, central lumen 102 accommodates the guidewire and is enlarged to provide a compartment 104. The compartment accommodates a cartridge 106 having an axially extended wall 108, a proximal end wall 110 and a distal end wall 112. A drive tube 114, connected to the proximal end wall, is manipulated at the housing to selectively position cartridge 106.

Drive tube 114 is used to rotate cartridge 106 about a longitudinal axis, rather than to move the cartridge axially. Consequently, while it requires less axial stiffness than drive rod 34, drive tube 114 must be resistant to torsional bending to apply the necessary torque to rotate cartridge 106. Also because of the lack of axial movement, compartment 104 need not extend proximally beyond window 116 to accommodate the cartridge length. As seen in FIGS. 11 and 12, cartridge wall 108 is open along a portion of its circumference, to provide an arcuate cartridge opening 118 defined by end walls 110 and 112 and axial edges 120 and 122. Axial edge 120 provides the cutting edge, and supports a linear cutting element 124. Cutting element 124 is flat and thin (e.g. 0.015 inches thick), with a rectangular profile, to provide a lower profile cutting edge as compared to a wire.

FIGS. 13 and 14 illustrate the use of catheter 98 to remove a lesion 126 from an artery 128. The catheter is positioned to axially align window 116 with lesion 126, and further to angularly align the window and lesion. A control knob (not shown but similar to knob 58) is turned rather than pushed or pulled, to angularly align cartridge 106 such that opening 118 coincides with window 116 (FIG. 13). At this point, band 100 is flexed to urge the catheter upwardly against the arterial wall whereby a portion of lesion 126 enters compartment 104.

At this point, the knob is turned to rotate cartridge 106 clockwise as viewed in FIG. 13 while cutting element 124 is heated, thus to progressively cut the lesion. Cartridge rotation continues until cutting edge 120 is carried beyond the clockwise edge of window 116, which closes the window and captures acquired tissue. Then, catheter 98 is proximally withdrawn to remove captured tissue, or a plunger is used to remove tissue from the cartridge.

FIG. 15 illustrates an alternative embodiment cartridge 130 having an axial wall that is open at the distal end and along part of its circumference to define two cutting edges 132 and 134. A continuous wire 136 (0.030 inch diameter) is mounted to the cartridge and shaped to provide an arcuate segment 138 mounted to cutting edge 132, and a linear segment 140 along axial cutting edge 134. Accordingly, cartridge 130 can be used to effect axial cutting and arcuate cutting. Cartridge wall 142 is continuous over at least sixty percent of its circumference to enable axial and angular positioning that closes the associated catheter window, to insure capture of severed tissue. Drive member 144 can be a tube, rod or coil and has sufficient axial and torsional rigidity to impart axial and rotational movement to the cartridge.

FIG. 16 illustrates an alternative circuit for heating an arcuate cutting element 146. A conductor 148 connects the cutting element with an RF power supply 150. A second conductor 152 couples the power supply and an indifferent electrode 154. The indifferent electrode preferably is an electrode plate, typically applied to the back of the patient. The power supply provides an RF signal to the cutting element via conductor 148. The signal returns to the power supply via conductor 152. Between cutting element 146 and indifferent electrode 154, current flows through body tissue. Consequently, ohmic heating of tissue is the primary factor in raising the temperature of tissue adjacent the cutting element to the predetermined or desired level. Cutting element 146 preferably is platinum, for high biocompatability and electrical conductivity. Accordingly cutting element heating from the current, while present to a degree, is slight compared to the ohmic heating effect. A controller 156 governs power supply 150 to provide the appropriate current in cutting element 146. While not shown in FIG. 16, a thermocouple or other sensing element can be mounted at the cutting element, to sense the temperature of the cutting element and adjacent tissue, and provide feedback to controller 156. As noted above, this approach (highly conductive cutting element and indifferent electrode) is presently the most preferred.

While the disclosure has focused on the treatment of coronary arteries, it is to be appreciated that devices in accordance with the present invention can be used to treat peripheral arteries and other vessels. These principles further can be applied in constructing and utilizing devices in neurology for removal of lesions in the carotid arteries, in gynecology for recanalization of Fallopian tubes, and in urology for removal of benign prostrate hyperplasia. The heating of the cutting element and adjacent tissue provides a fine, accurate cut to sever tissue at minimal risk of forming fragments, and provides a sealing action believed to reduce the incidence of restonosis. The cartridge can be either rotated or moved axially of the catheter, for greater versatility in severing unwanted tissue. After the cut, the cartridge completely closes the tissue-admitting window of the catheter, to insure complete capture of severed tissue.

What is claimed is:

1. A device for removing atheromas from a body lumen; including:

an elongate catheter having a proximal end and a distal end, a catheter wall defining a compartment within the catheter near the distal end, and an window through the catheter wall to allow entry into the compartment;

an electrically conductive tissue cutting element;

a carrier mounted movably relative to the catheter, for supporting the cutting element proximate the window for a controlled movement thereof along and adjacent the window; and a heating means for generating an electrical current in the cutting element to heat the cutting element at least to a selected temperature above normal body temperature, and for maintaining the cutting element at least at said selected temperature during said controlled movement;

wherein the catheter is flexible and maneuverable to locate the distal tip of the catheter within a body lumen and to place the window against a tissue wall segment of the body lumen to acquire tissue within the compartment, and the cutting element, when so heated and undergoing the controlled movement, severs the acquired tissue and heats tissue adjacent the cutting element while severing.

2. The device of claim 1 wherein:

said cutting element, when so heated and undergoing the controlled movement, further tends to cauterize a region of the cut.

3. The device of claim 1 wherein:

the carrier includes a cartridge contained within the compartment, said cartridge having an axially extended cartridge wall, a cartridge opening for receiving tissue into the cartridge, and a cutting edge that supports the cutting element; and wherein the carrier further includes a control means coupled to the cartridge and operable to selectively position and move the cartridge within the compartment, thus to provide said controlled movement.

4. The device of claim 3 wherein:

an axial dimension of the cartridge wall is greater than an axial dimension of said window, whereby the cartridge is positionable to substantially close the window.

5. The device of claim 3 wherein:

said cutting edge is a distal edge of the cartridge, and the cartridge is moved distally to provide said controlled movement of the cutting element.

6. The device of claim 3 wherein:

said cartridge is cylindrical and coaxial with the catheter, said axially extended cartridge wall is annular and open along a portion of its circumference to form the cartridge opening, and the cutting edge is an axial edge of the cartridge wall; and wherein the control means rotates the cartridge to move the cutting element along an arcuate cutting path.

7. The device of claim 3 wherein:

the control means comprises an elongate drive member connected to the cartridge and running along the catheter from the cartridge to the proximal end of the catheter, said drive member movable at said proximal end to impart like motion to the cartridge.

8. The device of claim 1 wherein:

the cutting element comprises a wire.

9. The device of claim 8 wherein:

the wire has a circular profile and is constructed of one of the following materials: nickel, a nickel chromium alloy, and platinum.

10. The device of claim 8 wherein:

the wire has a rectangular profile with a width of the wire being substantially greater than a thickness of the wire.

11. The device of claim 1 wherein:

the means for generating electrical current in the cutting element include a power supply, and first and second electrical conductors coupled to the power supply and coupled respectively to opposite ends of the cutting element.

12. The device of claim 11 further including:

a temperature sensing means for detecting the temperature of the cutting element.

13. The device of claim 11 wherein:

the power supply is either a DC power supply or an RF power supply, and is controllable to vary the amount of current in the cutting element.

14. The device of claim 1 wherein:

the means for generating electrical current in the cutting element include an RF power source, first and second conductors connected to the RF power source, an indifferent electrode, means electrically coupling the first electrode to the cutting element, and means electrically coupling the second conductor to the indifferent electrode, and wherein said heating of the cutting element and adjacent tissue is primarily due to ohmic heating of said tissue.

15. The device of claim 1 further including:

an infusion lumen in said catheter for supplying treatment agents through the catheter to the body lumen in a region about the distal end of the catheter.

16. The device of claim 1 wherein:

said window is positioned along a distal region of the catheter for lateral entry of tissue into the compartment, and the catheter includes a means for urging the window laterally against the tissue wall segment.

17. The device of claim 16 wherein:

the means for urging the window include a dilatation balloon mounted along the distal region, axially aligned with and on the opposite side of the catheter from the window, and means for inflating the balloon.

18. The device of claim 16 wherein:

the means for urging the window include a flexible band axially aligned with and on the opposite side of the catheter from the window.

19. A device for removing unwanted tissue from a body lumen; including:

an elongate catheter having a proximal end and a distal end, a catheter wall defining a compartment within the catheter near the distal end, and a window through the catheter wall to allow entry into the compartment;

a cartridge mounted movably within the compartment, said cartridge having a cartridge wall, a cartridge opening for receiving tissue into the cartridge, and a cutting edge along the cartridge opening;

a control means coupled to the cartridge and operable to selectively position and move the cartridge within the compartment, for providing a controlled movement of the cutting edge along and adjacent the window; and a heating means for heating the cutting edge at least to a selected temperature above normal body temperature, and for maintaining the cutting element at least at said selected temperature during said controlled movement;

wherein the catheter is flexible and maneuverable to locate the distal end of the catheter within a body lumen and to place the window against a tissue wall segment to acquire tissue within the compartment, and the cutting edge, when undergoing the controlled movement, severs the acquired tissue and heats adjacent tissue while severing; and wherein said control means is operable to move the cartridge between an open position for permitting entry into the compartment via the window, and a closed position in which the cartridge wall closes the window.

20. The device of claim 19 wherein:

the cutting edge is part of said cartridge wall and leads the cartridge wall when undergoing said controlled movement, whereby the cartridge is moved into the closed position substantially as severance of the acquired tissue is complete.

21. The device of claim 20 wherein:

the cutting edge is a distal edge of the cartridge, and the controlled movement of the cutting edge is in the distal direction.

22. The device of claim 20 wherein:

the cartridge is cylindrical and substantially coaxial with the catheter, the catheter wall extends axially and is open along a portion of its circumference to form the catheter opening, and the cutting edge comprises an axial edge of the catheter wall along the opening; and wherein the control means rotates the cartridge whereby said controlled movement of the cutting edge is arcuate.

23. The device of claim 19 wherein:

the control means includes a drive member connected to the cartridge and contained within a lumen of the catheter, said drive member being movable near the proximal end of the catheter to impart like movement to the cartridge.

24. The device of claim 19 wherein:

said heating means includes an electrically conductive tissue cutting element mounted along the cutting edge, and a means for generating an electrical current in the cutting element to heat the cutting element and said adjacent tissue at least to said selected temperature.

25. The device of claim 24 wherein:

the means for generating an electrical current in the cutting element include a power supply, and first and second electrical conductors coupled to the power supply and coupled respectively to opposite ends of the cutting element.

26. A process for removing tissue from a body lumen; including:

providing, near a distal end of an elongate catheter, a compartment and a window to the compartment through a catheter wall of the catheter, and an electrically conductive tissue cutting element mounted to the catheter for a controlled movement of the cutting element adjacent and along the window;

inserting the catheter into a body lumen, and guiding the catheter to position the window against a tissue wall segment of the body lumen, thus to cause tissue to enter the compartment via the window and occupy the compartment;

heating the cutting element heat adjacent tissue and to at least to a selected temperature above normal body temperature, and causing the cutting element while so heated to undergo said controlled movement, thereby to sever the tissue occupying the compartment.

27. The process of claim 26 further including:

after severing the tissue, closing the compartment to prevent egress of the severed tissue.

28. The process of claim 26 wherein:

said controlled movement of the cutting element tends to cauterize tissue in a region of the cut.

29. The process of claim 26 wherein:

the controlled movement of the cutting element is substantially linear and axial with respect to the catheter.

30. The process of claim 26 wherein:

the controlled movement of the cutting element is arcuate, about an axis running longitudinally of the catheter.

* * * * *